United States Patent
Su et al.

(10) Patent No.: US 7,333,849 B1
(45) Date of Patent: Feb. 19, 2008

(54) VERTICAL FIELD NEUROVASCULAR ARRAY COIL

(75) Inventors: Sunyu Su, Hudson, OH (US); Mark Xueming Zou, Aurora, OH (US); Jeff Kitzmiller, University Heights, OH (US)

(73) Assignee: General Electric Company, Schenectady, NY (US)

( * ) Notice: Subject to any disclaimer, the term of this patent is extended or adjusted under 35 U.S.C. 154(b) by 1089 days.

(21) Appl. No.: 10/186,032

(22) Filed: Jun. 28, 2002

Related U.S. Application Data

(63) Continuation-in-part of application No. 10/098,268, filed on Mar. 15, 2002, now Pat. No. 6,768,303, and a continuation-in-part of application No. 10/085,347, filed on Feb. 27, 2002, now Pat. No. 7,221,974.

(60) Provisional application No. 60/302,185, filed on Jun. 29, 2001, provisional application No. 60/276,297, filed on Mar. 16, 2001, provisional application No. 60/273,092, filed on Mar. 2, 2001.

(51) Int. Cl.
*A61B 5/055* (2006.01)
(52) U.S. Cl. ............. 600/422; 324/318; 324/322
(58) Field of Classification Search ......... 600/410, 600/421–422; 324/307, 309, 318, 322
See application file for complete search history.

(56) References Cited

U.S. PATENT DOCUMENTS

| | | | |
|---|---|---|---|
| 4,825,162 A | 4/1989 | Roemer et al. | |
| 5,517,120 A | 5/1996 | Misic et al. | |
| 5,578,925 A | 11/1996 | Molyneaux et al. | |
| 5,592,088 A * | 1/1997 | Matsunaga et al. | 324/318 |
| 5,621,323 A * | 4/1997 | Larsen | 324/318 |
| 6,377,836 B1 * | 4/2002 | Arakawa et al. | 600/422 |
| 6,577,888 B1 * | 6/2003 | Chan et al. | 600/422 |

OTHER PUBLICATIONS

P.B. Roemer et al., "The-NMR Phased Array," Magn. Reson. Med, 1990, 16, pp. 192-225.
Leussler et al., Improvement of SNR at Low Field Strength Using Mutually Decoupled Coils for Simultaneous NMR Imaging,: SMRM 1990 Annual Meeting Proceedings, p. 724.
D.I. Hoult et al., "Quadrature Detection in the Laboratory Frame," Magn. Reson. Med, 1984, 1, pp. 339-353.
J. Wang, "A Novel Method to Reduce the Signal Coupling of Surface Coils for MRI," ISMRM 1996 Annual Meeting Proceedings, p. 1434.

* cited by examiner

*Primary Examiner*—Ruth S. Smith
(74) *Attorney, Agent, or Firm*—The Small Patent Law Group LLP; Dean D. Small

(57) ABSTRACT

A vertical field MRI RF coil array for neurovascular imaging includes a head section having a solenoid coil element and a quadrature coil element; a neck section having a solenoid coil element and a quadrature coil element; and a chest section having a solenoid coil element and a quadrature coil element.

15 Claims, 7 Drawing Sheets

(2a) Chest saddle (2b) Neck saddle (2c) Head saddle

VERTICAL FIELD NEUROVASCULAR ARRAY COIL

CROSS-REFERENCE TO RELATED APPLICATIONS

This application claims the benefit of U.S. provisional patent applications Ser. No. 60/302,185 filed Jun. 29, 2001, Ser. No. 60/276,297 filed Mar. 16, 2001, and Ser. No. 60/273,092 filed Mar. 2, 2001.

This application is a continuation-in-part of U.S. patent application Ser. No. 10/085,347 filed Feb. 27, 2002 issued as U.S. Pat. No. 7,221,974 and Ser. No. 10/098,268 filed Mar. 15, 2002, issued as U.S. Pat. No. 6,768,303.

BACKGROUND OF THE INVENTION

The present invention relates to magnetic resonance imaging (MRI) and, in particular, to radio frequency (RF) coils.

MRI has been widely used by radiologists as a powerful diagnostic tool. MRI techniques have several advantages including excellent soft tissue viewing and angiography. Neurovascular MRI has become a standard diagnostic procedure in the hospitals. Frequently, a neurovascular MRI protocol requires imaging coverage from the Circle of Willis to the aortic arch with a field-of-view (FOV) of about 36 cm. Another imaging protocol with a smaller FOV for high resolution carotid imaging is of great interest also. Finally, it would be a plus if the same neurovascular coil could be used for head/neck imaging. An ideal neurovascular RF coil would provide multiple imaging modes with different FOV, good S/N, good uniformity, and a patient friendly structure.

The concept of a co-planar array (Roemer et al., U.S. Pat. No. 4,825,162) has been widely used in neurovascular coils for horizontal field systems. Typically, partially overlapped surface coils are placed in a co-planar fashion to extend the coverage as required by neurovascular imaging protocols. Multi-mode imaging is achieved by activating different combinations of coil elements. Coil isolation between neighboring elements is achieved through the well known overlapping technique to cancel the mutual inductance. Coil isolation between elements other than immediate neighbors is achieved through the application of low noise amplifiers (LNA) in the resonance circuits.

The principle of MRI involves exciting protons and detecting their free induction decay signals. Each proton possesses a tiny magnetic moment precessing about the static magnetic field. The macroscopic behavior of millions of protons can be represented by a resultant magnetization vector aligning with the static magnetic field $B_0$. A strong RF excitation pulse effectively tips the magnetization away from $B_0$. The free induction decay of this magnetization is detected in a plane perpendicular to $B_0$. Thus the normal direction of an receive RF coil must be perpendicular to the direction of the static magnetic field $B_0$ for maximal signal induction.

As a result, co-planar array coils are effective for horizontal MRI systems. However, such co-planar surface array coils are, in general, inefficient for a vertical field system because the condition required for maximal signal detection can hardly be fulfilled. Various modifications to the co-planar designs have been proposed with limited success.

A more effective array configuration is needed for a vertical field neurovascular coil to provide good S/N with multi-imaging modes.

SUMMARY OF THE INVENTION

A vertical field MRI RF coil array for neurovascular imaging includes a head section having a solenoid coil element and a quadrature coil element; a neck section having a solenoid coil element and a quadrature coil element; and a chest section having a solenoid coil element and a quadrature coil element.

DESCRIPTION OF THE PREFERRED EMBODIMENTS

An array formed of coaxial solenoid coil elements can be effective in a vertical field system. Solenoidal coils have the advantage of good sensitivity, uniformity and naturally fit to various body parts for a vertical field system.

The challenge for solenoid based coil arrays lies in the decoupling between solenoidal coil elements. Effectively suppressing the "cross-talk" between active coil elements is a requirement in order to take advantage of high efficiency arrays through simultaneous acquisition of multiple coil elements.

Advanced coils using uneven counter-rotational (UCR) coil based solenoidal arrays (Su et al., U.S. patent application Ser. No. 10/085,347 issued as U.S. Pat. No. 7,221,974 and double counter-rotational (DCR) coils (Su et al., 10/098,268 issued as U.S. Pat. No. 6,768,303 have proven successful. These applications are incorporated herein by reference. These coils exhibit inherent decoupling between neighboring solenoid coil elements. A UCR may be, for example, a solenoid coil formed of current loops with current flowing in the same direction and a counter rotational current loop, with uneven number of turns for the two sections. A UCR coil produces a quasi-one-peak sensitivity profile and a null-$B_1$ point at one side, through the uneven winding of its two sections. A second solenoid coil element can be placed near the null-$B_1$ point of a UCR coil to form an inherently decoupled solenoidal array.

A DCR coil may be, for example, a solenoid coil formed of a series of current loops with a counter rotational current loop on each of the two ends of the solenoid. A DCR coil produces a quasi-one-peak sensitivity profile and two null-$B_1$ points, one on each side of the coil. An additional solenoid coil can be placed near each one of the two null-$B_1$ points to form an inherently decoupled solenoidal array. A DCR coil can be used as the building block to form solenoidal arrays of multiple solenoid coil elements.

Figure 1:
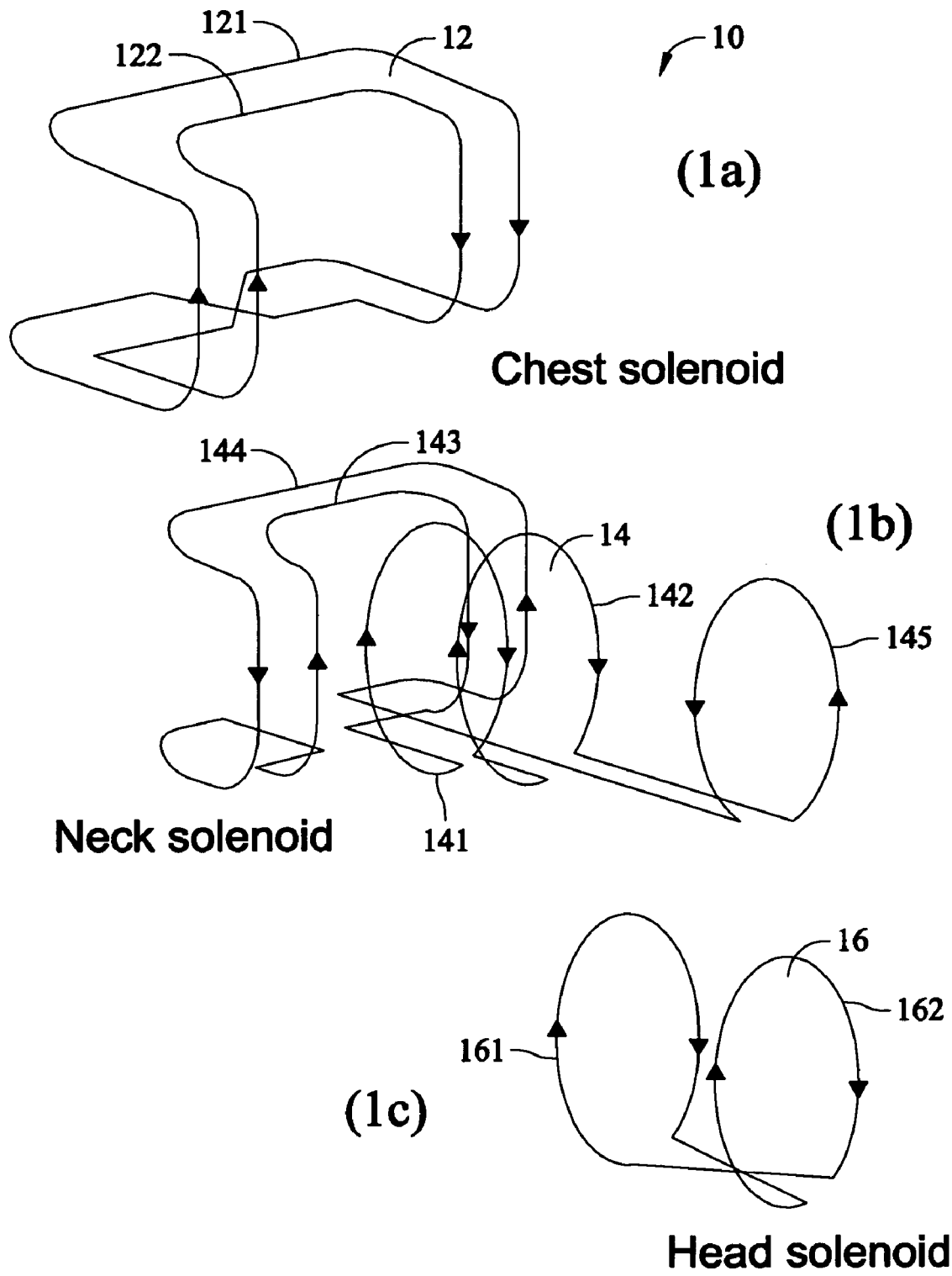
FIG. 1 is a schematic depiction of three solenoid coil elements according to the invention.
Figure 2:
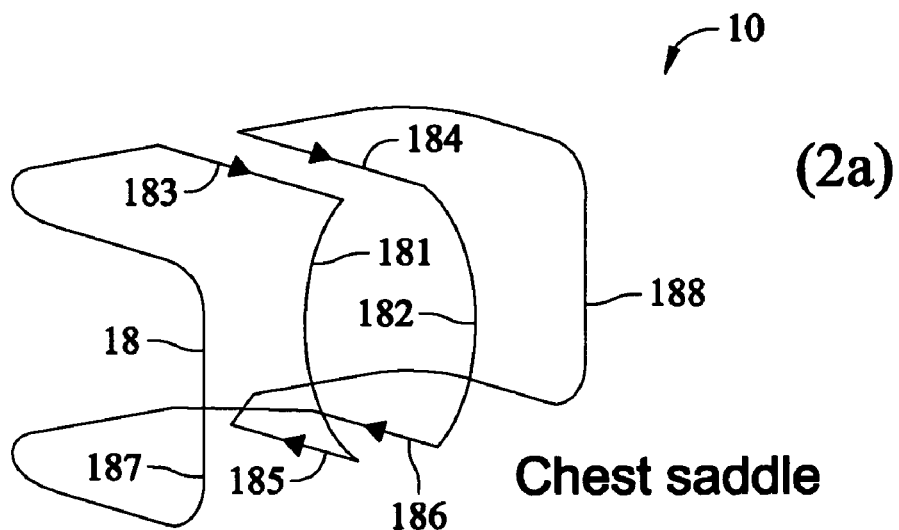
FIG. 2 is a schematic depiction of three saddle coil elements according to the invention.
Figure 2:
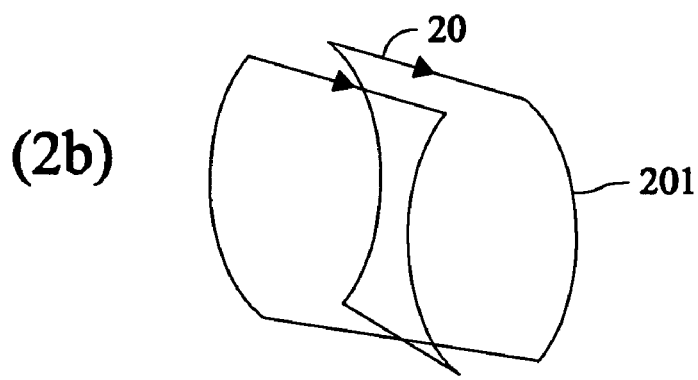
Figure 2:
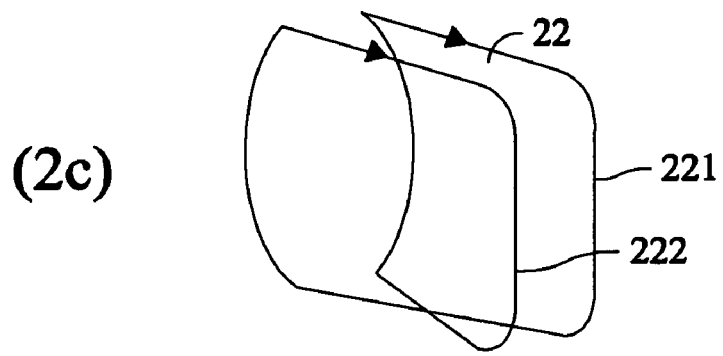

Referring FIGS. 1 and 2, a neurovascular coil array 10 may include six coil elements 12, 14, 16, 18, 20, 22 in the form of three solenoid-saddle orthogonal pairs (elements 12, 18, elements 14, 20 and elements 16, 22). The three coil element pairs are placed along the three anatomic regions of a human patient, the head, the neck and the chest. Each solenoid-saddle pair can be interfaced to two separate receivers or combined by quadrature detection to a single receiver as system hardware permits.

The three solenoid elements are shown in FIG. 1. The chest solenoid element 12 may be formed from two loops 121, 122 running over either side of the shoulder and wrapping around the chest and the back to improve signal reception in the aortic arch region, as shown in FIG. 1a. The neck solenoid element 14 may be be formed from three current loops 141, 142, 143 centered in the neck region of the patient, and two counter rotational loops 144, 145, one at the chest and one at the head, as shown in FIG. 1b. The head solenoid element 16 may be formed from a two current loops 161, 162. The chest solenoid 12 and head solenoid 16 are each been placed near one of the null $B_1$ points of the neck solenoid element 14 to achieve inherent coil decoupling.

The three saddle coil elements 18, 20, 22 are shown in FIG. 2. The chest saddle coil element 18 may be formed from a pair of arc conductors 181, 182 around the neck , a pair of parallel conductors 183, 184, 185, 186 in the chest and the back, and return conductors 187, 188 running over the shoulder to allow an open-arm coil structure. The neck saddle coil element 20 may be formed from a typical saddle coil 201. The head saddle coil element 22 may be formed from a modified saddle coil with a pair of conductors 221, 222 running over the head for improved sensitivity in that region. Coil isolation between neighboring saddle elements may be achieved by the overlapping technique as is known in the art (e.g., Roemer et al., U.S. Pat. No. 4,825,162).

The neurovascular coil array 10 takes into consideration the MRI system limitations and clinic neurovascular diagnostics needs. Presently, most of the commercial vertical MRI systems provide a useable imaging area of about 40 cm×40 cm due to magnet uniformity and gradient linearity limitations. Clinical studies show that a FOV of about 36 cm is appropriate for neurovascular imaging from the Circle of Willis to the aortic arch.

Based on the above considerations, the neurovascular coil 10 is provided with the capability of multiple imaging modes by selectively activating the coil elements. In a neurovascular imaging mode, the chest element pair 12, 18 and the neck element pair 14, 20 are activated while the head element pair 16, 22 is deactivated, providing about 36 cm FOV coverage from the Circle of Willis to the aortic arch. In a head/neck imaging mode, the head element pair 16, 22 and the neck element pair 14, 20 are activated while the chest element pair 12, 18 is deactivated, providing a 32 cm FOV. Other imaging modes are possible by activating only one of the three element pairs at a time in the head, neck or chest region. The smaller FOV allows higher resolution imaging of a particular anatomic region.

Figure 3:
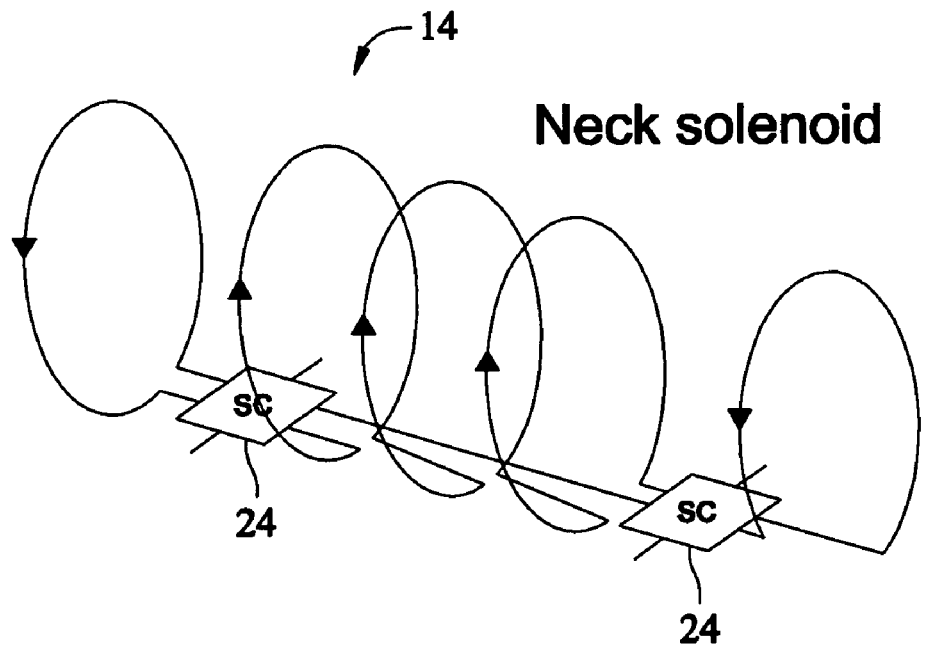
FIG. 3 is a schematic depiction of a neck coil element with switching circuits according to the invention and detail of one such circuit.
Figure 3:
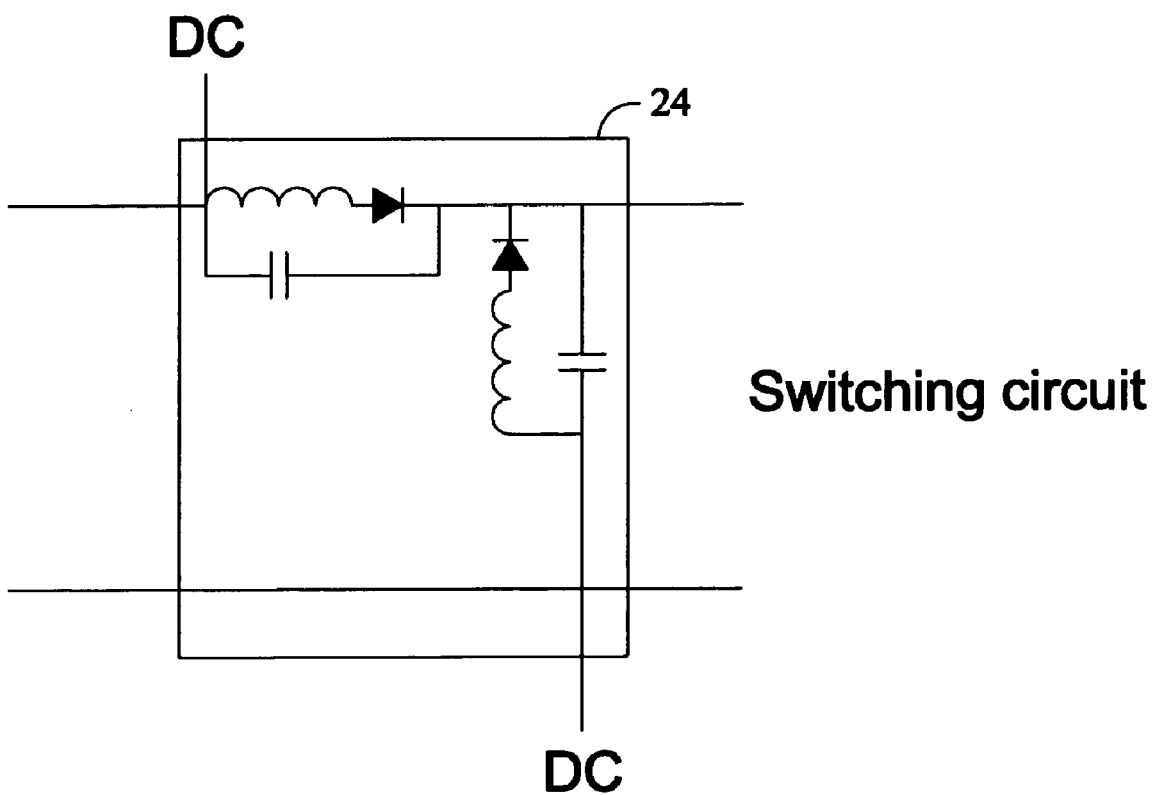

Referring to FIG. 3, in the preferred embodiment, the neck solenoid element 14 includes switching circuits 24 for operating in different modes. Switching is achieved by applying DC voltage to activate/deactivate PIN diodes in a resonant LC circuit. A parallel LC resonant circuit exhibits high impedance to block current flow effectively.

In a neurovascular imaging mode, the counter rotational loop 145 near the head is switched off. At the same time, the counter rotational loop 144 in the chest side provides a null-$B_1$ point as needed for decoupling with the chest solenoid element 12. This effectively operates the DCR coil in a UCR mode. In a head/neck imaging mode, the counter rotational loop 144 near the chest is switched off whereas the counter rotational loop 145 in the head side provides a null-$B_1$ point as needed for decoupling with the head solenoid element 16. This effectively operates the DCR coil in another distinct UCR mode.

Figure 4:
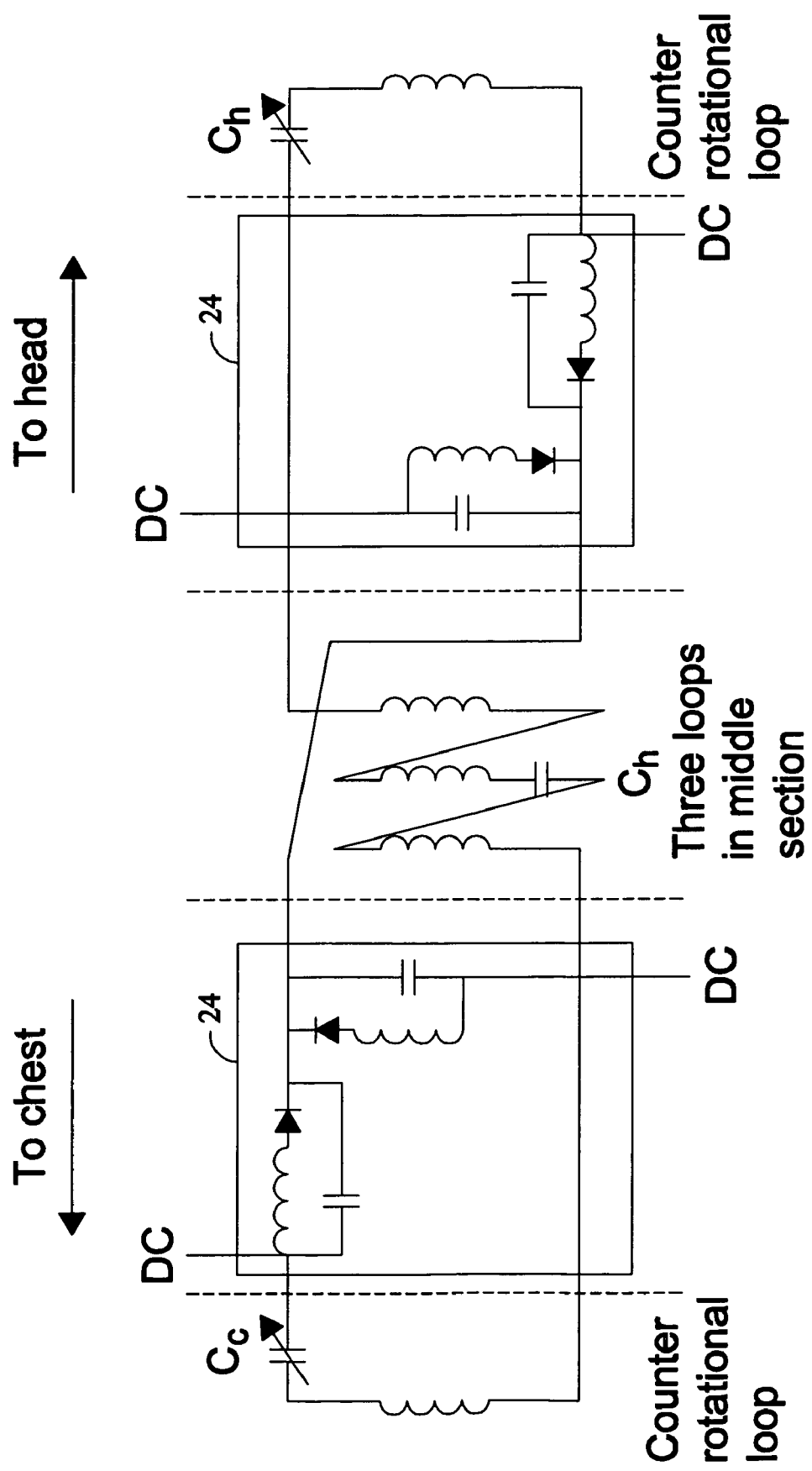
FIG. 4 is a detailed schematic diagram of neck coil element according to the invention.

The capability of tuning the DCR coil in two distinct UCR modes is depicted in FIG. 4. For head imaging UCR mode, tuning can be achieved by adjusting variable cap $C_h$ in the head region counter rotational loop. For a neurovascular imaging UCR mode, tuning can be achieved by adjusting variable cap $C_c$ in the chest region counter rotational loop.

It is also possible to switch off both counter rotational loops such that the element becomes a 3-turn "normal" solenoid in a neck-only imaging mode. The tuning can be achieved by selecting a proper value for $C_n$.

The multiple-mode imaging with different FOVs is advantageous and is achieved in this neurovascular coil design by implementing three coil element pairs or sections to cover three anatomic regions, the head, the neck and the chest. Due to its superior sensitivity and uniformity, a solenoid type coil element has been the preferred design for vertical field system. The ability to include three solenoid coil elements in this neurovascular coil is advantageous. This can be made possible by using a DCR coil for achieving inherent coil decoupling between neighboring solenoid coils.

Figure 5:
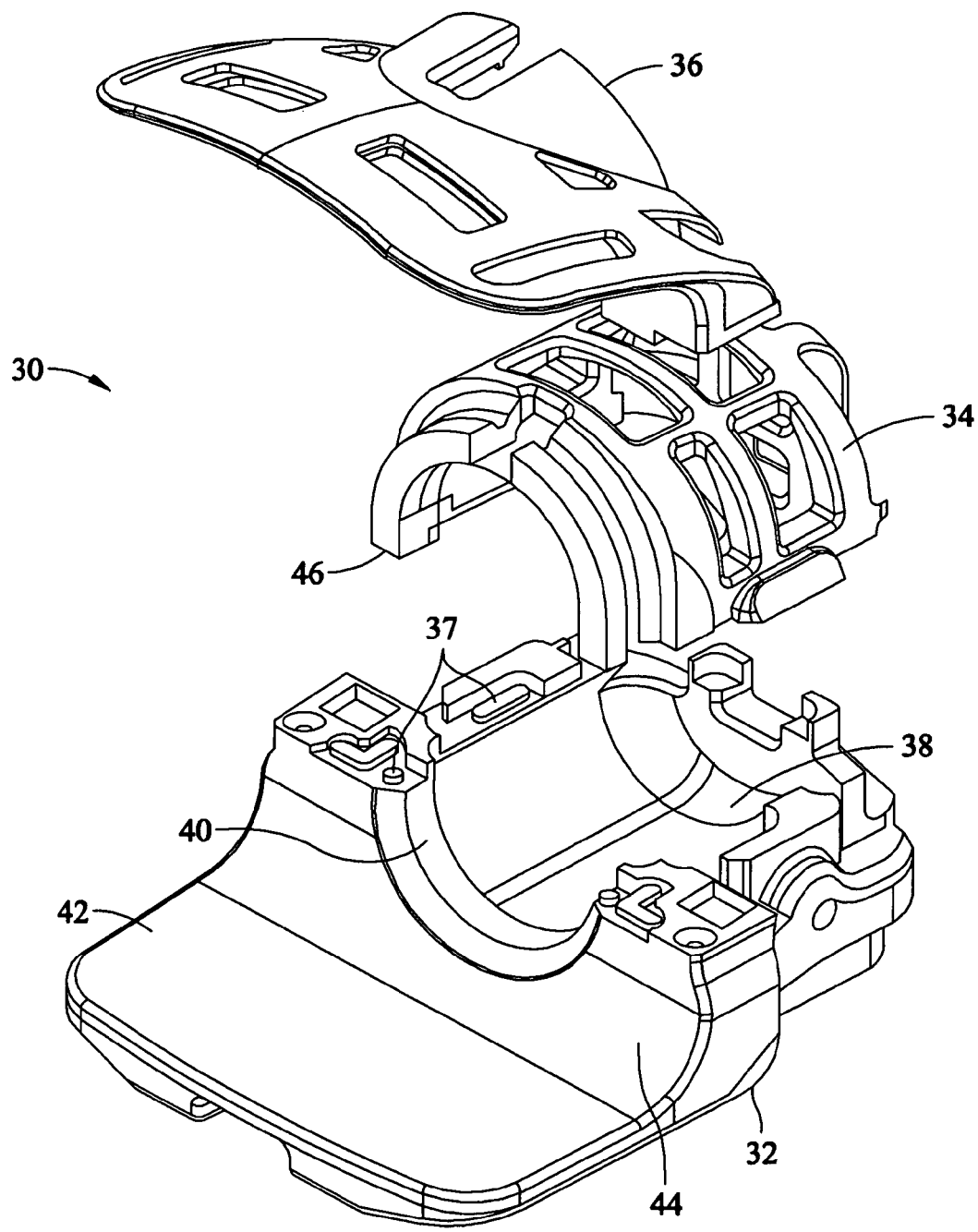
FIG. 5 is an exploded perspective view of a housing for a coil according to the invention.
Figure 6:
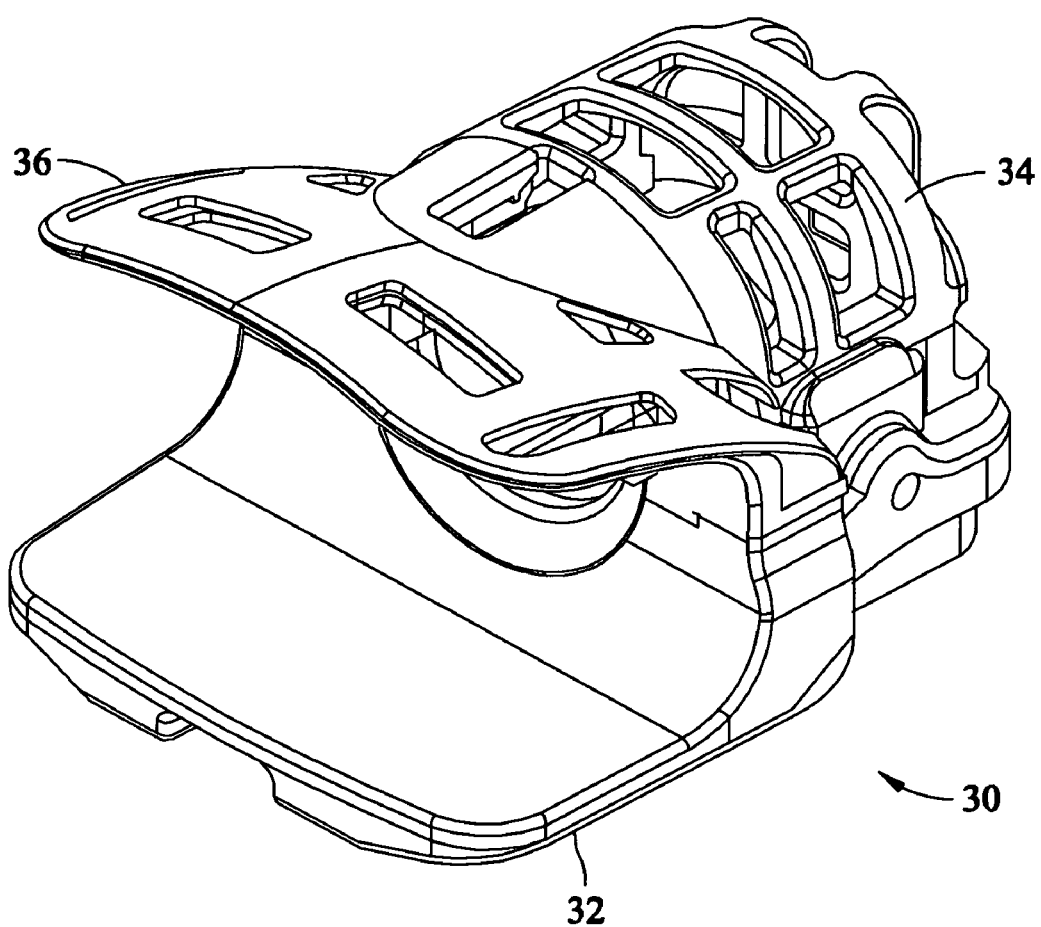
FIG. 6 is a perspective view of a housing for a coil according to the invention.
Figure 7:
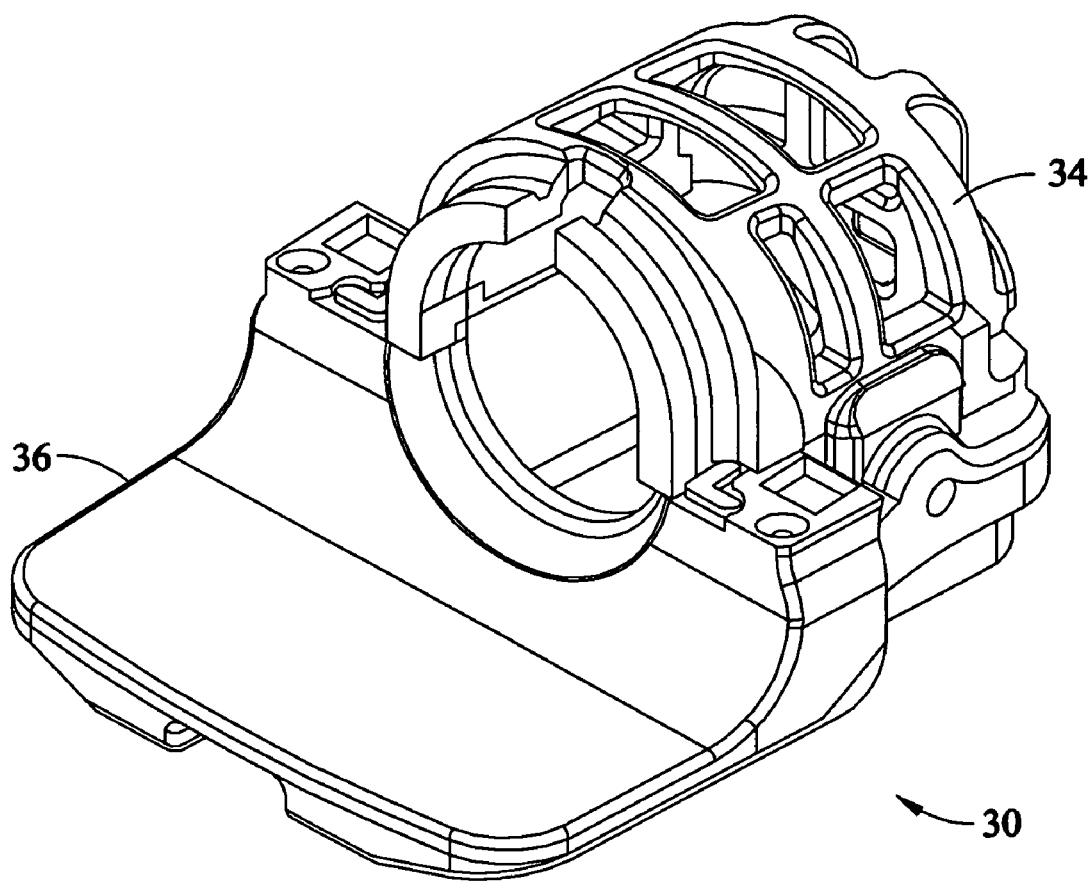
FIG. 7 is a perspective view of a partially assembled housing for a coil according to the invention.

Referring to FIGS. 5-7, the coil housing 30 for the coil array 10 may include three separate but integrateable parts, a base 32, a split head-top 34 and a detachable chest-top 36. Note that connectors (e.g., connectors 37) are used to provide electrical connection between the tops and the base. FIG. 6 shows the parts assembled. FIG. 7 shows the coil with the chest piece detached, a configuration that can be used for head/neck imaging.

It can be seen from FIG. 5 that the base 32 includes a semi-cylindrical structure in the head region 38, a narrower and smaller neck region 40 and a flat structure in the back region 42. The shoulder region 44 is contoured to better fit the body. The top surface of the coil base 32 provides support for the patient, whereas the space underneath provides room for coil trace and coil circuit electronic components.

FIG. 5 also shows that the head-top 34 includes a semi-cylindrical structure in the head region with windows in the eyes and mouth area, a narrower and smaller neck region and an extension piece 46 to accommodate additional coil trace for a better coverage toward the chest. Coil trace and electronic components are installed between the interior and exterior covers.

It can be seen from FIG. 6 that the chest-top 36 is a sectional thin structure with interior and exterior covers and a thin gap in between for installation of coil trace and electronic components. The chest-top 36 is cut off at the arms to eliminate restrictions to the arms of larger patients. The feature can be seen most clearly from FIG. 6. In case of head/neck imaging, the coil trace associated with the chest piece is inactive. Therefore, the imaging can be performed with the chest piece detached, as shown in FIG. 7.

Various modifications can be made to the basic form of invention as discussed above. The number of solenoid coil elements is not limited to three, as many solenoid elements can be included in the array as needed by, for example, using DCR type solenoid coil elements as a building block.

The saddle coil elements can be replaced with other types of coil elements as needed provided that the produced $B_1$ field is orthogonal to the axial $B_1$ field generated by the solenoid element. These can be referred to generally as a quadrature coil element.

Variations to the mechanical design are also possible. For example, instead of a split head-top, a sliding head-top can be implemented to meet the preference of some patients. More and larger windows can be implemented to optimize the openness and further reduce patient claustrophobia. Instead of having a single base piece, it is also possible to separate the head base portion and make it a sliding head design. In this case, a head holder can be used as a head support. The shape of the chest-top can be optimized to better fit the body and achieve optimal signal reception. Different sizes array coils can be made to accommodate patients of different sizes.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A vertical field MRI RF coil array for neurovascular imaging, said array comprising:
    a head section having a solenoid coil element and a quadrature coil element;
    a neck section having a solenoid coil element and a quadrature coil element;
    a chest section having a solenoid coil element and a quadrature coil element and wherein the solenoid coil element comprises two loops each configured to extend over at least one side of a shoulder to be imaged from a chest to a back to be imaged.

2. An array according to claim 1, wherein said neck section solenoid coil element includes an at least two turn solenoid coil element.

3. An array according to claim 2, wherein said neck section coil element further comprises a counter rotational solenoid coil element at each end of said at least two turn solenoid coil element.

4. An array according to claim 3, further comprising a switching element between at least one of said counter rotational solenoid coil elements and said at least two turn solenoid coil element, said switching element being operable to connect/disconnect said at least one of said counter rotational solenoid coil elements to said at least two turn solenoid coil element.

5. An array according to claim 1, wherein said head section solenoid coil element is an at least two turn solenoid coil.

6. An array according to claim 1, wherein said chest section solenoid coil element is an at least two turn solenoid coil.

7. An array according to claim 1, wherein said quadrature coil elements are saddle coil elements.

8. An array according to claim 1, wherein at least one of said sections includes an electrically and physically removable portion adapted to allow easy placement of a patient for imaging.

9. An array according to claim 1, wherein said neck section solenoid coil element includes variable tuning capacitors and said variable tuning capacitors are configured to be adjustable to provide different null-$B_1$ points.

10. An array according to claim 1, further comprising a variable capacitor in the head section.

11. An array according to claim 1, further comprising a variable capacitor in the chest section.

12. An array according to claim 1, wherein said neck section solenoid coil element includes counter rotational loops and said counter rotational loops comprise double counter-rotational (DCR) coils.

13. An array according to claim 1, further comprising a switching circuit configured to operate said head section, neck section and chest section in one of a plurality of different modes.

14. An array according to claim 13, wherein the different modes comprise different tuning modes.

15. An array according to claim 1, wherein the neck section solenoid coil element includes counter rotational loops and variable tuning capacitors configured to decouple at least one of the chest section solenoid coil element and the head section solenoid element.

* * * * *